United States Patent
Maruyama et al.

(10) Patent No.: US 6,417,167 B1
(45) Date of Patent: Jul. 9, 2002

(54) LYOPHILIZED COMPOSITIONS CONTAINING SHINGOGLYCOLIPID AND PROCESS FOR PREPARING THEM

(75) Inventors: Kazutoshi Maruyama; Hideaki Nomura, both of Takasaki; Akihiko Takeuchi, Maebashi, all of (JP)

(73) Assignee: Kirin Beer Kabushiki Kaisha, Tokyo-to (JP)

( * ) Notice: Subject to any disclaimer, the term of this patent is extended or adjusted under 35 U.S.C. 154(b) by 0 days.

(21) Appl. No.: 09/897,992

(22) Filed: Jul. 5, 2001

Related U.S. Application Data

(63) Continuation of application No. 09/147,099, filed as application No. PCT/JP98/00462 on Feb. 4, 1998, now abandoned.

(30) Foreign Application Priority Data

Feb. 5, 1997 (JP) ................................. 9-22585

(51) Int. Cl.⁷ .......................... A61K 31/70; C07H 17/02
(52) U.S. Cl. ......................................... 514/25; 536/17.9
(58) Field of Search ............................ 514/25; 536/17.9

(56) References Cited

U.S. PATENT DOCUMENTS 5,767,092 A   6/1998   Koezuka et al. ............... 514/25

FOREIGN PATENT DOCUMENTS

| JP | 50-71816 | 11/1973 |
|----|----------|---------|
| JP | 49-4933 | 2/1974 |
| JP | 50-5523 | 1/1975 |
| JP | 54-157818 | 12/1979 |
| JP | 60-190711 | 9/1985 |
| JP | 60-239417 | 11/1985 |
| JP | 63-115816 | 5/1988 |
| JP | 1-132514 | 5/1989 |
| JP | 1-299232 | 12/1989 |
| JP | 5-508640 | 12/1993 |
| JP | 6-271598 | 9/1994 |
| JP | 8-245418 | 9/1996 |

*Primary Examiner*—James O. Wilson
*Assistant Examiner*—Leigh C. Maier
(74) *Attorney, Agent, or Firm*—Foley Lardner

(57) ABSTRACT

The object of the present invention is to improve the solubility of sphingoglycolipids having low solubility in water. Disclosed is a lyophilized composition comprising the α-glycosylceramide represented by the following formula (A) or a salt thereof, a polyoxysorbitan fatty acid ester and disaccharide or monosaccharide, and preferably additional deoxycholic acid or histidine, and a process for preparing it:

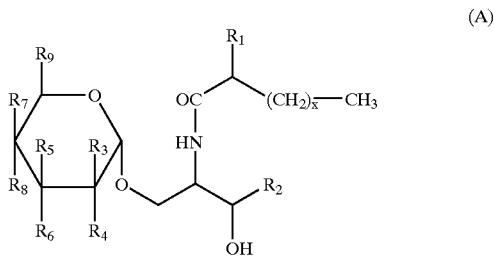

wherein $R_1$ represents H or OH;

X denotes an integer in the range of 7–25;

$R_2$ represents any one of the substituents —$CH_2(CH_2)_YCH_3$, —$CH(OH)(CH_2)_YCH_3$, —$CH(OH)(CH_2)_YCH(CH_3)_2$, —$CH=CH(CH_2)_YCH_3$, or —$CH(OH)(CH_2)_YCH(CH_3)CH_2CH_3$, wherein Y denotes an integer in the range of 5–17; either one of $R_3$ or $R_4$ represents H, and the other represents H, OH, $NH_2$ or $NHCOCH_3$; either one of $R_5$ or $R_6$ represents H, and the other represents OH; either one of $R_7$ or $R_8$ represents H, and the other represents OH; $R_9$ represents H, $CH_3$ or $CH_2OH$.

12 Claims, 2 Drawing Sheets

LYOPHILIZED COMPOSITIONS CONTAINING SHINGOGLYCOLIPID AND PROCESS FOR PREPARING THEM

This is a Continuation Application of application Ser. No. 09/147,099, filed Oct. 5, 1998 now abandoned which is a 37 of PCT/JP98/00462.

TECHNICAL FIELD

The present invention relates to lyophilized compositions containing sphingoglycolipid, and more particularly to lyophilized compositions containing sphingoglycolipid, in which the sphingoglycolipids intrinsically having low or little solubility into water have been improved in their solubility into water, and the process for preparing them.

BACKGROUND ART

α-sphingoglycolipids exhibit a variety of useful physiological activities in body, and may be used for numerous medical agents such as anti-tumor agents, immunostimulators, and bone marrow cell proliferating promoters.

Amongst the sphingoglycolipids, most of the ones comprising monosaccharide as the sugar moiety are of low or little solubility in water. Various methods have been examined in order to improve the solubility of such sphingoglycolipids, resulting in unsatisfactory solubility. There is a problem in these methods that solution of the sphingoglycolipids in water preciptates during their storage thereby decreasing the solubility with the passage of time.

DISCLOSURE OF THE INVENTION

In view of such circumstances as above, the object of the present invention is to provide a lyophilized composition comprising a low or little soluble sphingoglycolipid sugar moiety of which is composed of a monosaccharide and maintaining a high re-solubility even after storage for a long period.

The present inventors have found that when a sphingoglycolipid ((α-glycosylceramide) which has α-glycosyl linkage structure comprising a monosaccharide as a sugar moiety and a low solubility in water was lyophilized after incorporation to be dissolved in a solvent together with a polyoxysorbitan fatty acid ester and sucrose (white sugar), mannitol or glucose, or alternatively further comprising sodium deoxycholate or histidine, the composition has an extremely high re-solubility still after storage for a long period. The present invention has been accomplished on the basis of the finding.

That is to say, the present invention relates to a lyophilized composition comprising the α-glycosylceramide as an active ingredient represented by the following formula (A) or a salt thereof, a polyoxysorbitan fatty acid ester and sucrose, mannitol or glucose, or alternatively further comprising sodium deoxycholate or histidine:

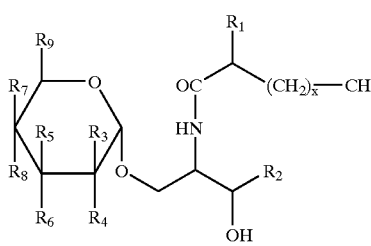

wherein $R_1$–$R_9$ and X represent a particular group and an integer in the particular range described hereinafter, respectively.

The present invention also relates to a process for preparing the lyophilized composition which comprises dissolving the components incorporated in the composition in a heated aqueous solvent, cooling and then subjecting the solution to the step of lyophilization.

BEST MODE FOR CARRYING OUT THE INVENTION

[Compound Represented by the Formula (A)]

The compound used in the composition according to the present invention is as described above the compound having the α-glycosylceramide structure represented by the formula (A), in which X and $R_1$–$R_9$ are defined described below.

In the preferred embodiment, the above-described compound is the α-glycosylceramide represented by the formula (A').

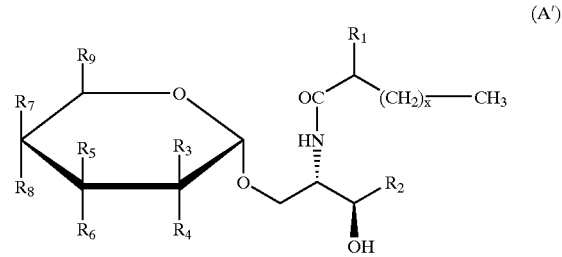

wherein $R_1$, $R_2$ and X have the same meanings as defined above, and $R_3$–$R_9$ represent the substituents defined in the following i) -v):

i)
   when $R_3$, $R_6$ and $R_8$ represent H,
   $R_4$ represents H, OH, $NH_2$ or $NHCOCH_3$, $R_5$ represents OH,
$R_7$ represents OH,
$R_9$ represents H, $CH_3$ or $CH_2OH$;

ii)
when $R_3$, $R_6$ and $R_7$ represent H,
$R_4$ represents H, OH, $NH_2$ or $NHCOCH_3$,
$R_5$ represents OH,
$R_8$ represents OH,
$R_9$ represents H, $CH_3$ or $CH_2OH$;

iii)
when $R_4$, $R_6$ and $R_7$ represent H,
$R_3$ represents H, OH, $NH_2$ or $NHCOCH_3$,
$R_5$ represents OH,
$R_8$ represents OH,
$R_9$ represents H, $CH_3$ or $CH_2OH$;

iv)
when $R_4$, $R_5$ and $R_7$ represent H,
$R_3$, $R_6$ and $R_8$ represent OH,
$R_9$ represents H, $CH_3$ or $CH_2OH$;

v)
when $R_3$, $R_5$ and $R_7$ represent H,
$R_4$, $R_6$ and $R_8$ represent OH,
$R_9$ represents H, $CH_3$ or $CH_2OH$.

The preferred α-glycosylceramide compound used in the present invention is the one having the sugar moiety in the formula (A) in which $R_3$, $R_6$ and $R_8$ represent H, $R_4$, $R_5$ and $R_7$ represent OH, and $R_9$ represents $CH_2OH$, and the ceramide moiety in which $R_2$ represents substituent (b), (c) or (e) containing an OH, particularly (b). In the preferred compounds described above, the compounds having the ceramide moiety in which $R_1$ represents H and $R_2$ represents (b) are more preferred. In addition, X of methylene in the alkyl group of the ceramide moiety preferably denotes the integer in the range of 11–25, more preferably in the range of 21–25, and Y in the group $R_2$ preferably denotes the integer in the range of 9–17, more preferably in the range of 11–15.

Figure 2:
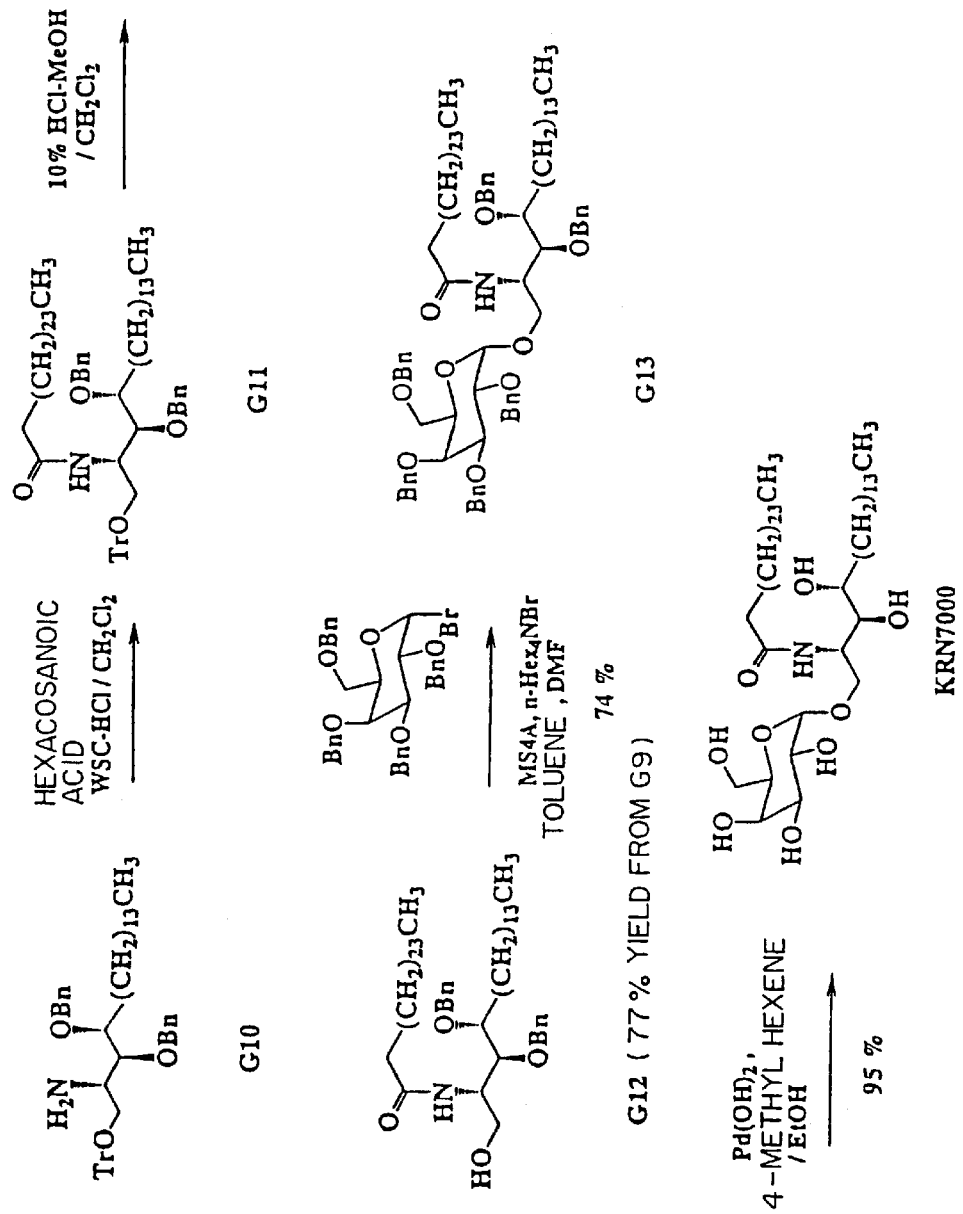
FIG. 2 is a diagram illustrating a synthetic reaction route following FIG. 1, in which reaction route WSC-HCl represents 1-ethyl-3-(3'-dimethyl-aminopropyl)carbodiimide hydrochloride, MS4A represents Molecular Sieves 4A, and $Hex_4NBr$ represents tetrahexylammonium bromide.

Among the α-glycosylceramide used in the present invention, (2S,3S,4R)-1-(α-D-galactopyranosyloxy)-2-hexacosanoylamino-3,4-octadecanediol is the particularly preferred compound and referred to hereinafter as KRN7000 (see FIG. 2 as to the structural formula).

The compound represented by the formula (A) may include an acid adduct salt thereof. The compounds used in the present invention include the adduct salts thereof.

Acids with which the acid adduct salts are formed include for example inorganic acids such as hydrochloric acid, sulfuric acid, nitric acid, phosphoric acid, and organic acids such as acetic acid, propionic acid, maleic acid, oleic acid, palmitic acid, citric acid, succinic acid, tartaric acid, fumaric acid, glutamic acid, pantothenic acid, laurylsulfonic acid, methanesulfonic acid and phthalic acid.

In addition, it is a matter of course that when an acid addition salt is used as a pharmaceutical agent, the acid must be a pharmaceutically acceptable one.

The active component compound used in the present invention can be prepared by any methods appropriate for the synthesis of an α-glycosylceramide.

Some of the α-glycosylceramide compounds are described together with the methods for synthesizing them in WO93/5055, WO94/2168 and WO94/9020, and can be prepared according to the methods. Also, as the preferred method, there is illustrated in the Examples mentioned hereinafter a method for synthesizing the compound KRN7000, that is a method for synthesizing the ceramide moiety starting from D-lyxose and bonding galactose as the sugar moiety to the ceramide thus synthesized (see the Examples hereunder and FIGS. 1 and 2 as to the details). The objective compound can be synthesized according to the method. In addition, the general synthesis method of α-glycosylceramides is disclosed for example in J. Med. Chem., 38, 2176 (1995).

[Lyophilized Composition and Method for Preparing it]

The lyophilized composition according to the present invention can be used for such applications as injections and as culture medium for cell therapy using an aqueous solvent such as water or a buffer solution.

The α-glycosylceramide compound as the active component used in the composition of the present invention has a variety of physiological activities, and the present composition can be used for injections (including instillation) as the medicinal agents such as anti-tumor agents, immunostimulators (see WO93/5055), and bone marrow cell proliferating promoters (see Japanese Patent Laid-Open Publication No. WO94/2168), treatment agents for autoimmune diseases, and peripheral blood stem cell proliferating agents. Also, the lyophilized composition according to the present invention can be used for cell therapy, for example for a large volume suspension of cells or culture medium in the antigen presenting cell therapy (Yamaguchi, Y. et al., Oncol. Res., 8, 399 (1997)), the tumor therapy or the like in which an antigen presenting cell, a cancer cell or the like is cultured, activated in vitro and returned to body.

The lyophilized composition according to the present invention comprises the above-described α-glycosylceramide or a salt thereof, a polyoxysorbitan fatty acid ester, and disaccharide or monosaccharide (including their combination) incorporated therein, and is excellent in solubility in water after lyophilization and after storage for a long period. In addition, the re-solubility after storage for a long period can be further improved by additionally incorporating sodium deoxycholate or histidine (including their combination) into the above formulation.

The polyoxysorbitan fatty acid ester includes Polysorbate 20, Polysorbate 40, Polysorbate 60, Polysorbate 80 and the like, and Polysorbate 20 is preferred. It is incorporated preferably in an amount of 10–1,000 parts by weight, more preferably 20–100 parts by weight on the basis of 1 part by weight of the active compound. The disaccharide includes sucrose, lactose, maltose and the like, among which sucrose is particularly preferred. The monosaccharide includes glucose, fructose, xylitol, sorbitol, mannitol and the like, among which glucose and mannitol are particularly preferred. These saccharides are incorporated preferably in an amount (total amount in the case of combination) of 100–10,000 parts by weight, more preferably 200–2,000 parts by weight on the basis of 1 part by weight of the active compound. In addition, sodium deoxycholate and histidine are incorporated preferably in an amount (total amount in the case of combination) of 10–1,000 parts by weight, more preferably 20–400 parts by weight.

As to components to be incorporated, there may be added, in addition to the above-described basic components, additives such as a dissolution aid such as polyoxyethylene hydrogenated castor oil 60, a buffer such as phosphate, an isotonic agent such as sodium chloride, an analgesic agent such as benzyl alcohol, if necessary.

The lyophilized composition according to the present invention can be prepared fundamentally by dissolving the above-described components to be incorporated in an appropriate solvent such as distilled water by heat stirring, followed by cooling and lyophilizing the solution. That is to say, the process for preparing the lyophilized composition according to the present invention comprises dissolving the above-described components to be incorporated in a heated aqueous solvent, cooling and then subjecting the solution to the step of lyophilization.

The aqueous solvent includes distilled water, physiological saline, buffer, and the like.

In the above-described process, the components to be incorporated are dissolved in a solvent heated usually at a temperature in the range of 65–90° C., preferably 70–85° C. If the heating temperature is too high, the storage stability of the incorporated components is lowered; if the temperature is too low, the components are hardly dissolved. The solution thus obtained is cooled usually at a temperature lowering rate of 0.5° C.–1.0° C./min or more, or cooled rapidly at a temperature lowering rate of preferably 1.5° C./min or more, more preferably 2.0° C./min or more, most preferably 4.0° C./min or more. The solution is usually cooled in a circulating incubator to a temperature of 50–40° C. or less, preferably about 20–30° C., then filtered and lyophilized. Cooling in a shorter time will further stabilize the re-solubility after storage for a long period.

Lyophilization process can be carried out with a container such as ampoule or vial and a lyophilization apparatus according to the conventional method, preferably under the condition of a freezing temperature at −20° C. or less and of a degree of vacuum at 0.1 Torr or less.

The composition of the present invention thus prepared in its use as injection is administered to a body as a pharmaceutical agent for injection in the form of solution reconstituted, when the composition is used, in an appropriate amount of a solvent for injection, usually distilled water, physiological saline or the like (the concentration of α-glycosylceramide being usually in the range of 0.1–1,000 μg/ml).

The composition of the present invention can be administered via any appropriate dosage routes, specifically in the case of animals, intraperitoneally, subcutaneously, intravascularly, e.g. intravenously or intraarterially, topically or the like, and in the case of human, intravenously, intraarterially, topically, intraperitoneally, intrathoracically, subcutaneously, intramuscularly, or the like.

The dosage of the composition of the present invention for injection is determined in consideration of the individual situation so that the total dosage administered continuously or intermittently does not exceed the predetermined amount. It is needless to say that the specific dosage varies depending upon the dosage routes, situations of a patient such as age, body weight, sex, sensitivity, administration time for meal (feed), combined pharmaceutical agents, the patient or severity of disease. Furthermore, suitable dosage and frequency under a certain condition must be determined on the basis of the above-described instructions by the dosage finding test of professional physicians. The dosage of the effective component in the composition of the present invention required for expressing its activity is, for example, in the range of about 0.001–10 mg per day in adult human in the case of intravenous administration.

In addition, in the non-injection uses such as antigen presenting cell therapy, tumor therapy or the like, the composition of the present invention is reconstituted in a culture medium containing an aqueous solvent (distilled water, physiological saline, buffer, and the like) to culture in the solution the antigen presenting cells (such as dendritic cells) or the cells intended to enhance the immunogenicity (such as tumor cells) thus resulting in in vitro contact of the cells with the composition of the present invention so as to enhance the antigen presenting activity or the immunogenicity. By way of example, the composition of the present invention can be added to the cell culturing medium in such an amount as the final concentration of α-glycosylceramide to be in the range of 0.1–10,000 ng/ml (preferably 10–1,000 ng/ml) to culture the cells for 12 hours-14 days for enhancing the antigen presenting activity or the immunogenicity of the cells. The cells whose antigen presenting activity or the immunogenicity has been enhanced can be administered by the conventional methods in the form of injection, suspension, emulsion or the like via a variety of conventional dosage routes (such as intravenous, intraarterial or subcutaneous administration).

EXAMPLES

The Examples of the present invention are described below, which is not intended to limit the invention.

The α-glycosylceramide used as the active component in the lyophilized composition of the present invention have, as described above, a variety of physiological activities such as anti-tumor activity, immuno-stimulating activity, bone marrow cell proliferation promoting activity or antigen presenting activity enhancing activity.

[Preparation Example of the Compound]

Preparation of α-glycosylceramide

Figure 1:
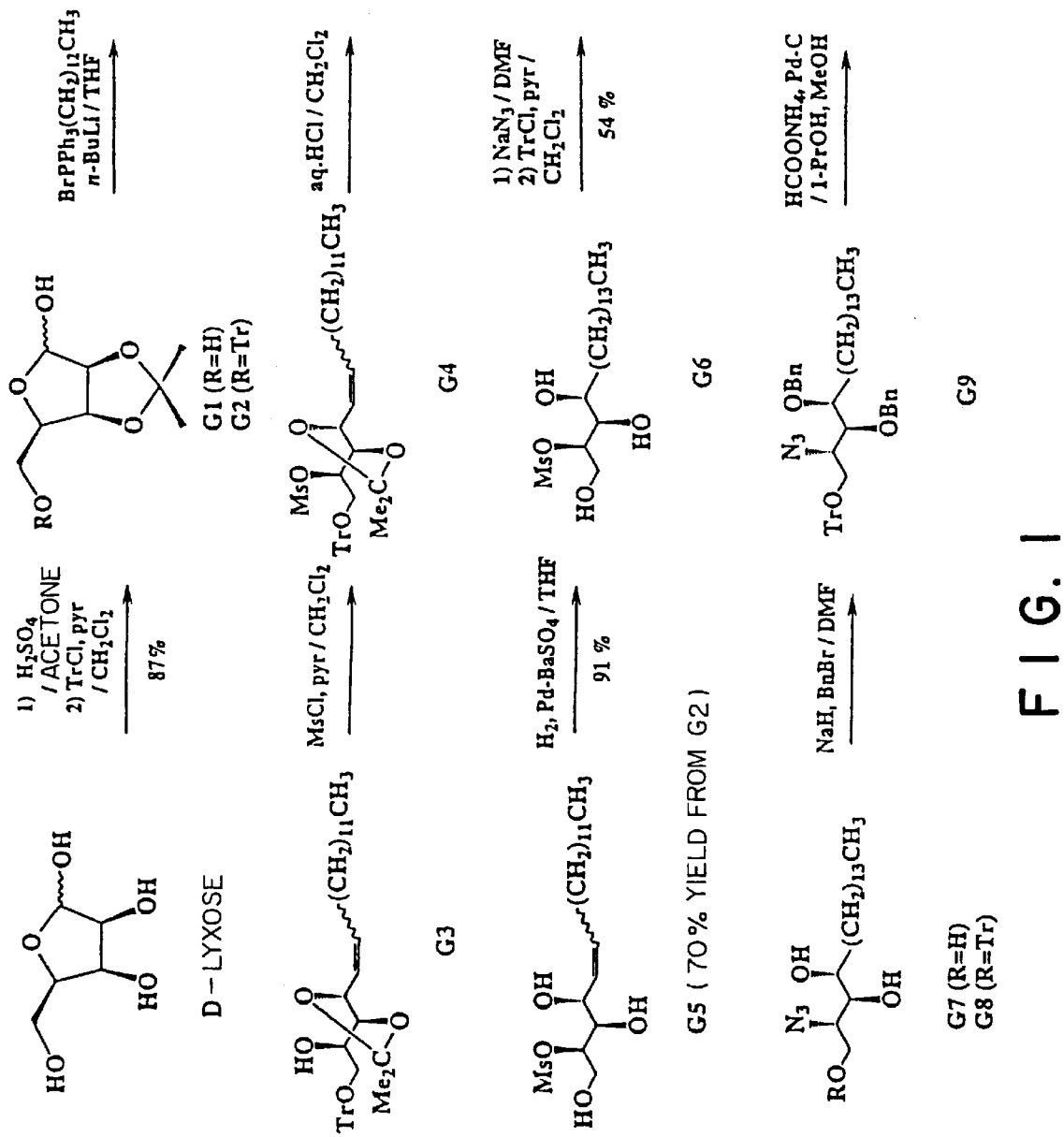
FIG. 1 is a diagram illustrating a synthetic reaction route of a typical example of the α-glycosylceramide compounds (KRN 7000) used in the present invention, in which reaction route pyr represents pyridine, $BrPPh_3(CH_2)_{12}CH_3$ represents tridecanetriphenylphosphonium bromide, n-BuLi represents n-butyl lithium, MsCl represents methanesulfonyl chloride, BnBr represents benzyl bromide, and 1-PrOH represents propyl alcohol.

Synthesis example of KRN7000 as a representative example of α-glycosylceramide is described below (see FIGS. 1 and 2).

(1) Synthesis of the Compound G1

To a solution of D-lyxose (200 g, 1.33 mole) in acetone dehydrated with calcium chloride (3.0 L) was added sulfuric acid (0.5 ml), and the mixture was stirred at room temperature for 18 hours. After neutralization with powdery Molecular Sieves 4A, the reaction mixture was filtered through celite, and the residue was washed with acetone. The filtrate and the wash were combined and concentrated under reduced pressure to give the crude product of G1 in a yield of 240 g (95%). The product was used for the subsequent steps without further purification. The analytical sample was purified by silica gel chromatography with an eluting solvent of hexane: acetone (9:1).

mp 76–78° C.; FDMS m/z 191 (M+1)$^+$; $^1$H-NMR (500 MHz, CDCl$_3$) δ5.45 (1H, d, J=1.8 Hz), 4.83 (1H, dd, J=3.7, 5.5 Hz), 4.64 (1H, d, J=6.1 Hz), 4.27–4.30 (1H, m), 3.90–3.99 (2H, m), 1.48 (3H, s), 1.32 (3H, s).

(2) Synthesis of the Compound G2

To a solution of the compound G1 (239 g, ca. 1.26 mmole) in methylene chloride (168 ml) were added pyridine (10 ml) and trityl chloride (39.0 g), and the mixture was stirred at 32° C. for 4 hours. Ethanol (8 ml) was added dropwise, and the mixture was stirred at room temperature for 2 hours. After washing with saturated aqueous ammonium chloride solution, saturated aqueous sodium hydrogen carbonate solution and brine, and the reaction mixture was concentrated under reduced pressure. The residue was dissolved in ethyl acetate and cooled to 0° C. for crystallization. Yield 501 g (87% from D-lyxose).

mp 174–176° C.; FDMS m/z 432 M$^+$; $^1$H-NMR (500 MHz, CDCl$_3$) δ7.21–7.49 (15H, m), 5.38 (1H, d, J=2.4 Hz), 4.75 (1H, dd, J=3.7, 6.1 Hz), 4.59 (1H, d, J=6.1 Hz), 4.31–4.35 (1H, m), 3.43 (1H, dd, J=4.9, 9.8 Hz), 3.39 (1H, dd, J=6.7, 9.8 Hz), 1.29 (3H, s), 1.28 (3H, s).

(3) Synthesis of the Compound G3

To a solution of tridecanetriphenylphosphonium bromide (962 g, 1.16 mole; prepared by heating 1-bromotridecane and triphenylphosphine at 140° C. for 4.5 hours) in THF (1500 ml) was added under argon dropwise a 2.5 M hexane solution of n-butyl lithium (462 ml; 366 mmole) at 0° C.

After dropwise addition, the mixture was stirred, and a solution of the compound G2 (250 g, 579 mmole) in THF (450 ml) was added dropwise. The mixture was heated gradually up to room temperature with stirring for 18 hours. The reaction mixture was concentrated under reduced pressure. The residue was diluted with a mixture of hexane:methanol:water (10:7:3, 1000 ml) and washed with saturated aqueous ammonium chloride solution. The aqueous layer was extracted with hexane (500 ml), and all of the organic layers were combined, dried over anhydrous magnesium sulfate, and concentrated under reduced pressure to give the crude product of G3. It was used directly for the subsequent step without further purification. Yield 339 g (98%). The analytical sample was purified by silica gel chromatography with an eluting solvent of hexane: ethyl acetate (9:1).

FDMS m/z 598 M$^+$; $^1$H-NMR (500 MHz, CDCl$_3$) δ7.21–7.45 (15H, m), 5.48–5.59 (2H, m), 4.91 (0.7H, t, J=7.3 Hz), 4.44 (0.3H, t, J=7.3 Hz), 4.26 (0.3H, dd, J=4.3, 7.3 Hz), 4.21 (0.7H, dd, J=4.3, 6.7 Hz), 3.75 (0.7H, m), 3.69 (0.3H, m), 3.24 (0.3H, dd, J=4.9, 9.8 Hz), 3.17 (0.7H, dd, J=4.9, 9.8 Hz), 3.09–3.14 [1H, (3.11, dd, J=4.9, 9.2 Hz), H1bE overlapped], 1.75–2.03 (2H, m), 1.49 (3H, s), 1.39 and 1.38 (3H, each s), 1.21–1.34 (20H, m), 0.88 (3H, t, J=6.7 Hz).

(4) Synthesis of the Compound G4

To a solution of the compound G3 (338 g, ca. 565 mmole) in methylene chloride (1500 ml) were added pyridine (500 ml) followed by methanesulfonyl chloride (49 ml, 633 mmole) dropwise, and the mixture was stirred at 31° C. for 24 hours. Ethanol (40 ml) was added dropwise, and the mixture was stirred at room temperature for 1 hour. After concentration under reduced pressure, the residue was diluted with a mixture of hexane:methanol:water (10:7:3, 1000 ml), and the layers were separated. The aqueous layer was extracted three times with hexane (200 ml), and all of the organic layers was combined, dried over anhydrous magnesium sulfate, and concentrated under reduced pressure to give the crude product of G4. It was used directly for the subsequent step without further purification. Yield 363 g (95%). The analytical sample was purified by silica gel chromatography with an eluting solvent of hexane:ethyl acetate (9:1).

FDMS m/z 676 M$^{30}$; $^1$H-NMR (500 MHz, CDCl$_3$) δ7.21 –7.47 (15H, m), 5.41 (0.7H, ddd, J=5.5, 9.2, 11.0 Hz), 5.32 (0.7H, bt, J=11.0 Hz), 5.22 (0.3H, bdd, J=9.2, 15.0 Hz), 5.02 (0.3H, dt, J$_t$=7.3 Hz, J$_d$=15.0 Hz), 4.8 (0.7H, ddd, J=3.1, 5.5, 7.9 Hz), 4.73 (0.7H, dd, J=5.5, 9.8 Hz), 4.64–4.67 (0.3H, m), 4.61 (0.3H, dd, J=5.5, 9.2 Hz), 4.48 (0.7H, dd, J=5.5, 7.9 Hz), 4.22 (0.3H, dd, J=5.5, 9.2 Hz), 3.55 (0.3H, dd, J=2.4, 11.6 Hz), 3.45 (0.7H, dd, J=3.2, 11.0 Hz), 3.06–3.12 [4H, (3.12, s), (3.11, s), (3.09, dd, J=3.1, 11.0 Hz)], 1.66–1.82 (2H, m), 1.47 and 1.46 (3H, each s), 1.39 (3H, s), 1.13–1.35 (20H, m), 0.88 (3H, t, J=6.8 Hz).

(5) Synthesis of the Compound G5

To a solution of the compound G4 (362 g, ca. 536 mmole) in methylene chloride (1500 ml) was added methanol (350 ml), then added dropwise concentrated hydrochloric acid (200 ml), and the mixture was stirred at room temperature for 5 hours. The reaction mixture was neutralized with sodium hydrogen carbonate, and filtered. The filtrate was concentrated under reduced pressure, and the residue was diluted with ethyl acetate and washed with brine. The aqueous layer was extracted with ethyl acetate, and all of the organic layers were combined, dried over anhydrous magnesium sulfate and concentrated under reduced pressure. The concentrate was crystallized from hexane. Yield 161 g (70% from G2).

mp 66–67° C.; FDMS m/z 377 (M–H$_2$O)$^+$; $^1$H-NMR (500 MHz, CDCl$_3$+D$_2$O) d 5.86 (0.3H, dt, J$_t$=7.3 Hz, J$_d$=14.7 Hz), 5.77 (0.7H, dt, J$_t$=7.3 Hz, J$_d$=10.4 Hz), 5.55 (0.3H, br.dd, J=7.3, 14.7 Hz), 5.49 (0.7H, bt, J=9.8 Hz), 4.91–4.97 (1H, m), 4.51 (0.7H, bt, J=9.8 Hz), 4.11 (0.3H, bt, J=7.3 Hz), 3.94–4.03 (2H, m), 3.67–3.73 [1H, (3.70, dd, J=3.1, 6.7 Hz), (3.69, dd, J=3.1, 7.3 Hz)], 3.20 and 3.19 (3H, each s), 2.05–2.22 (2H, m), 1.22–1.43 (20H, m), 0.88 (3H, t, J=6.7 Hz).

(6) Synthesis of the Compound G6

To a solution of the compound G5 (160 g, 405 mmole) in THF (780 ml) was added 5% palladium-barium sulfate (16 g), and reactor was purged with hydrogen gas, and the mixture was stirred at room temperature for 20 hours. The reaction mixture was filtered through celite, and washed with mixture of chloroform:methanol (1:1). The filtrate and the wash were combined and concentrated under reduced pressure. The residue was crystallized from ethyl acetate. Yield 146 g (91%).

[α]$^{23}_D$+12° (c1, CHCl$_3$/MeOH=1:1); mp 124–126° C.; FDMS m/z 397 (M+1)$^+$; $^1$H-NMR (500 MHz, CDCl$_3$+CD$_3$OD=1:1) δ4.93–4.96 (1H, m, H2), 3.91 (1H, dd, J=6.7, 12.2 Hz), 3.85 (1H, dd, J=4.9, 12.2 Hz), 3.54–3.60 (1H, m), 3.50 (1H, dd, J=1.8, 8.5 Hz), 3.19 (3H, s), 1.75–1.83 (1H, m), 1.53–1.62 (1H, m), 1.21–1.45 (24H, m), 0.89 (3H, t, J=6.7 Hz).

(7) Synthesis of the Compound G7

To a solution of the compound G6 (145 g, 365 mmole) in DMF (1000 ml) was added sodium azide (47 g, 730 mmole), and the mixture was stirred at 95° C. for 4 hours. The reaction mixture was concentrated, and the residue was diluted with ethyl acetate (450 ml) and washed with water. The aqueous layer was re-extracted with ethyl acetate. All organic layers were combined, washed with brine, dried over anhydrous magnesium sulfate and concentrated under reduced pressure to give the crude product of G7. Yield 122 g (97%). It was used directly for the subsequent step without further purification. Yield 126 g (95%). The analytical sample was purified by silica gel chromatography with an eluting solvent of hexane:ethyl acetate (9:1).

[α]$^{23}_D$+16.5° (c 0.5, CHCl$_3$–MeOH=1:1); mp 92–93° C.; FDMS m/z 344 (M+1)$^+$; $^1$H-NMR (500 MHz, CD$_3$OD) δ3.91 (1H, dd, J=3.7, 11.6 Hz), 3.75 (1H, dd, J=7.9, 11.6 Hz), 3.49–3.61 (3H, m), 1.50–1.72 (2H, m), 1.22–1.46 (24H, m), 0.90 (3H, t, J=6.7 Hz).

(8) Synthesis of the Compound G8

To a solution of the compound G7 (121 g, ca. 352 mmole) in methylene chloride (750 ml) were added pyridine (250 ml) and trityl chloride (124 g, 445 mmole), and the mixture was stirred at room temperature for 16 hours. After dropwise addition of ethanol (30 ml) and stirring at room temperature for 30 minutes, the reaction mixture was washed with saturated aqueous sodium hydrogen carbonate solution, saturated aqueous ammonium chloride solution and brine, dried over anhydrous magnesium sulfate, and concentrated under reduced pressure. The residue was purified by silica gel chromatography with an eluting solvent of hexane:ethyl acetate (10:1). Yield 34.4 g (52% from G6).

[α]$^{24}_D$+11.9° (c 0.9, CHCl$_3$); FDMS m/z 585 M$^{30}$; $^1$H-NMR (500 MHz, CDCl$_3$+D$_2$O) δ7.24–7.61 (15H, m), 3.62–3.66 (2H, m), 3.51–3.57 (2H, m), 3.42 (1H, dd, J=6.0, 10.4 Hz), 1.23–1.56 (26H, m), 0.88 (3H, t, J=6.7 Hz).

(9) Synthesis of the Compound G9

To a solution of the compound G8 (33.5 g, 57.3 mmole) in DMF (300 ml) was added 60% sodium hydroxide (5.5 g, ca. 138 mmole as NaH), and the mixture was stirred at room temperature for 40 minutes. The reaction mixture was cooled to 0° C., and benzyl bromide (15 ml, 120 mmole) was added dropwise. The reaction mixture was stirred for 18 hours while the temperature was raised gradually up to room temperature. Ice-water (100 ml) was added to the reaction mixture to stop the reaction, and the mixture was extracted with ethyl acetate. The extract was washed three times with brine, and all the organic layers were combined, dried over anhydrous magnesium sulfate, and concentrated under reduced pressure to give the crude product of G9. It was used directly for the subsequent step without further purification. Yield 42.2 g (96%). The analytical sample was purified by silica gel chromatography with an eluting solvent of hexane:ethyl acetate (100:1).

$[\alpha]^{24}_D$+9.8° (c 1.0, CHCl$_3$); FDMS m/z 738 (M-N$_2$)$^+$; $^1$H-NMR (500 MHz, CD$_3$OD) δ7.07–7.48 (25H, m), 4.57 (1H, d, J=11.6 Hz), 4.44 (1H, d, J=11.6 Hz), 4.41 (2H, s), 3.73–3.79 (1H, m), 3.46–3.56 (2H, m), 3.37 (1H, dd, J=8.6, 10.4 Hz), 1.20–1.64 (2,6H, m), 0.88 (3H, t, J=6.7 Hz).

(10) Synthesis of the Compounds G10 and G 11

To a solution of the compound G9 (41.2 g, ca. 54 mmole) in 1-propanol (250 ml) was added methanol (30 ml), followed by 5% palladium-carbon (4.1 g) and ammonium formate (27.1 g, 4.3 mole). The mixture was stirred at room temperature for 16 hours, diluted with ethyl acetate, and filtered through celite. The filtrate was concentrated under reduced pressureconstituted in ethyl acetate, washed three times with saturated aqueous sodium hydrogen carbonate solution and brine. All the organic layers were combined, dried over anhydrous magnesium sulfate, and concentrated under reduced pressure to give the crude product of GIO. Yield 38.9 g (98%). The product G10 thus obtained was directly used for the next step without further purification.

To a solution of the compound G10 in methylene chloride (300 ml) were added hexacosanoic acid (22.4 g, 56.5 mmole) and WSC hydrochloride (12.6 g, 64.6 mmole), and the mixture was heated with refluxing for 2 hours, cooled to room temperature, and concentrated under reduced pressure. The residue was diluted with ethyl acetate (500 ml), and washed with 0.5 M aqueous hydrochloric acid solution, brine, saturated aqueous sodium hydrogen carbonate solution, and finally with brine. All the organic layers were combined, dried over anhydrous magnesium sulfate, and concentrated under reduced pressure to give the crude product of G11. Yield 53.2 g (88%). The product G11 thus obtained was directly used for the next step without further purification. The analytical sample was purified by silica gel chromatography with an eluting solvent of hexane:ethyl acetate (100:1).

$[\alpha]^{24}_D$+5.3° (c 0.4, CHCl$_3$); FDMS m/z 1118 M$^{30}$ ; $^1$H-NMR (500 MHz, CDCl$_3$) δ7.20–7.38 (25H, m), 5.57 (1H, d, J=9.1 Hz), 4.80 (1H, d, J=11.6 Hz), 4.48–4.50 (3H, m), 4.24–4.32 (1H, m), 3.83 (1H, dd, J=3.0, 6.7 Hz), 3.43–3.51 (2H, m, H1a), 3.29 (1H, dd; J=4.3, 9.8 Hz), 1.92 (2H, t, J=7.3 Hz), 1.28–1.60 (72H, m), 0.88 (6H, t, J=6.7 Hz).

(11) Synthesis of the Compound G12

To a solution of the compound G11 (52.2 g, ca. 47 mmole) in methylene chloride (180 ml) were added methanol (36 ml), then added dropwise 10% hydrochloric acid-methanol solution (3.0 ml), and the mixture was stirred at room temperature for 2 hours. The reaction solution was neutralized with powdery sodium hydrogen carbonate (18 g), and filtered through celite. The residue was washed with methylene chloride. The filtrate and the wash were combined, washed with brine, and the organic layer was dried over anhydrous magnesium sulfate, and concentrated under reduced pressure. The residue was dissolved in acetone under heating, and purified by forming precipitation at 0° C. Yield 38.6 g (77% from G9).

$[\alpha]^{24}_D$−29.7° (c 0.7, CHCl$_3$); mp 75–76.5° C.; FDMS m/z 876 M$^{30}$ ; $^1$H-NMR (500 MHz, CDCl$_3$) δ7.30–7.47 (10H, m), 6.03 (1H, d, J=7.9 Hz), 4.72 (1H, d, J=11.6 Hz), 4.66 (1H, d, J=11.6 Hz), 4.61 (1H, d, J=11.6 Hz), 4.45 (1H, d, J=11.6 Hz), 4.12–4.17 (1H, m), 4.00 (1H, dt, J$_t$=4.3, J$_d$=7.3 Hz), 3.67–3.72 (2H, m), 3.61 (1H, ddd, J=4.3, 8.6, 11.6 Hz), 1.94–2.05 (2H, m), 1.15–1.69 (72H, m), 0.88 (6H, t, J=6.1 Hz).

(12) Synthesis of the Compound G13

1) 2,3,4,6 -tetra-O-benzyl-D-galactopyranosyl acetate (79.8 g) was dissolved in the mixed solvent of toluene (160 ml) and isopropyl ether (520 ml), and cooled to a temperature in the range of −10–0° C. An isopropyl ether solution containing 2.0 equivalents of HBr (2.8 mmole/ml, ca. 100 ml) was added to this mixture. After stirring at −10–0° C. for about 90 minutes, unreacted HBr in the reaction mixture was neutralized with 5% aqueous sodium hydrogen carbonate solution. The total volume of the mixture was separated in a separatory funnel, the aqueous layer was discarded, and the organic layer was washed twice with 10% aqueous sodium chloride solution, and concentrated under reduced pressure to give 2,3,4,6-tetra-O-benzyl-α-D-galactopyranosyl bromide (GalBr) in the form of syrup.

2) To a solution of the compound G12 (60.0 g, 68.6 mmole), tetrahexylammonium bromide (89.4 g, 206 mmole) and Molecular Sieves 4A (60 g) in toluene (420 ml) were added DMF (140 ml) followed by a solution of Ga1Br (ca. 137 ml) in toluene (250 ml), and the mixture was stirred at room temperature for 72 hours. Methanol (12 ml) was added to the reaction solution, and the mixture was stirred for 2 hours, filtered through celite, washed with saturated aqueous sodium hydrogen carbonate solution and brine, dried over anhydrous magnesium sulfate, and concentrated under reduced pressure. The residue was diluted with acetonitrile, and stirred for 2 hours to give precipitate. The precipitate thus obtained was dried under reduced pressure to give a dry powder. This product was purified by silica gel chromatography with an eluting solvent of hexane: ethyl acetate (8 1). Yield 70.9 g (74%)

$[\alpha]^{24}_D$+18.8° (c 0.9, CHCl$_3$); mp 74–75° C.; FDMS m/z 1399 (M+1)$^+$; $^1$H-NMR (500 MHz, CDCl$_3$) δ7.21–7.37 (30H, m), 6.12 (1H, d, J=9.0 Hz), 4.91 (1H, d, J=11.6 Hz), 4.84 (1H, d, J=3.7 Hz), 4.72–4.80 (4H, m), 4.35–4.65 (7H, m), 4.12–4.18 (1H, m), 3.99–4.05 (2H, m), 3.84–3.93 (4H, m), 3.73 (1H, dd, J=3.7, 11.0 Hz), 3.47–3.51 (2H, m), 3.42 (1H, dd, J=6.1, 9.1 Hz), 1.87–1.99 (2H, m), 1.18–1.70 (72H, m), 0.88 (6H, t, J=7.4 Hz).

(13) Synthesis of the Compound KRN7000

To a suspension of the compound G13 (60.0 g, 42.9 mmole) in ethanol (960 ml) was added a suspension of a 20% solution of palladium hydroxide (6.0 g) in ethanol, followed by 4-methylcyclohexene (120 ml, 93.5 mmole) as a hydrogen source, and the mixture was heated at reflux temperature for 4 hours, and filtered to remove the catalyst. The residue was washed with warmed ethanol. White precipitates obtained by leaving the filtrate standing at room temperature was filtered and dried under reduced pressure. The powdery product thus obtained was suspended in ethanol:water (92:8, 3.5 liters), dissolved by heating with stirring, then left standing at room temperature to form precipitates again. The precipitates were filtered, and the filtered cake was dried under reduced pressure to give a white powdery product. Yield 35.0 g (95%).

$[\alpha]^{23}_D$+43.6° (c 1.0, pyridine); mp 189.5–190.5° C.; negative FABMS m/z 857 (M−H)$^-$; IR (cm$^-$, KBr) 3300, 2930, 2850, 1640, 1540, 1470, 1070; $^1$H-NMR (500 MHz, C$_5$D$_5$N) δ8.47 (1H, d, J=8.5 Hz), 5.58 (1H, d, J=3.7 Hz), 5.27 (1H, m), 4.63–4.70 (2H, m), 4.56 (1H, m), 4.52 (1H, t, J=6.1 Hz), 4.37–4.47 (4H, m), 4.33 (2H, m), 2.45 (2H, t, J=7.3 Hz), 2.25–2.34 (1H, m), 1.87–1.97 (2H, m), 1.78–1.85 (2H, m), 1.62–1.72 (1H, m), 1.26–1.45 (66H, m), 0.88 (6H, t, J=6.7 Hz).

$^{13}$C-NMR (125 MHz, C$_5$D$_5$N) δ173.2 (s), 101.5 (d), 76.7 (d), 73.0 (d), 72.5 (d), 71.6 (d), 71.0 (d), 70.3 (d), 68.7 (t), 62.7 (t), 51.4 (d), 36.8 (t), 34.4 (t), 32.1 (t), 30.4 (t), 30.2 (t), 30.03 (t), 30.00 (t), 29.93 (t), 29.87 (t), 29.81 (t), 29.76 (t), 29.6 (t), 26.5 (t), 26.4 (t), 22.9 (t), 14.3 (q).

[Lyophilized Composition]

(1) Selection of a Solvent for the Active Component

Experimental Condition

First, 1 mg of the active component (KRN7000) was weighed and stirred in 100 ml of a variety of solvents (Table 3) in a heated bath to 80° C. for 20 minutes in order to form a solution having a concentration of 10 μg/ml. With respect to the solvents which were judged to have successfully dissolved 10 μg/ml of the active component, dissolution was further tried in the same manner as above in order to form a solution having a concentration of 100 μg/ml. With respect to the solvents which were judged to have successfully dissolved 100 μg/ml of the active component, dissolution was further tried in the same manner as above in order to form a solution having a concentration of 200 μg/ml. After cooling with running water, the solubility of the component was judged.

The solubility of the component was judged by the test described below. First, transparent colorless glass vials having a volume of 5 ml were charged with about 1.5 ml portion of each sample and sealed up. The vial was cleaned outside and placed beneath the white light source in a darkroom for observation with naked eye at the position of a luminous intensity of about 5,000 lux. When the sample was clear with no precipitates, it was judged that the active component was dissolved.

The results are shown in Table 3.

TABLE 3

| Solvents | Concentration of the active component (KRN7000) | | |
|---|---|---|---|
| | 10 μg/ml | 100 μg/ml | 200 μg/ml |
| Distilled water | + | | |
| 1N HCl | + | | |
| 1N NaOH | + | | |
| Propylene glycol | − | + | |
| Macrogol 400 | − | + | |
| Glycerol | − | + | |
| Ethanol | − | − | − |
| 0.5% Polysorbate 20 | − | − | − |
| 0.5% Polysorbate 80 | − | + | |
| 0.5% Cremophor | + | | |
| 0.5% HCO 50 | + | | |
| 0.5% HCO 60 | + | | |
| 0.5% Polyoxamer 188 | + | | |

Note)
Judgment of solubility (by naked eye):
+ not dissolved (or deposited),
− dissolved.

From the above results, ethanol or 0.5% Polysorbate 20 was contemplated as the solvent, but 0.5% Polysorbate 20 was selected as the solvent because of 100% ethanol being inappropriate for practical use.

(2) Examination of the Optimal Amount of the Additional Solvent

Experimental Condition

First, Polysorbate 20 was dissolved in distilled water in such concentrations as listed in Table 4. Next, 20 mg of the active component (KRN7000) was weighed and stirred in 100 ml of the Polysorbate solutions having a variety of concentrations in a heated bath at 80° C. for 20 minutes in order to form a solution. After cooling with running water, the mixture was filtered through a 0.22 μm filter, and transparent colorless glass vials having a volume of 5 ml were charged with a 2 ml portion of each of a variety of solutions and sealed up.

These samples were stored at 25° C. for 2 weeks, and judged of their solubility. The samples judged in solution were further stored, and judged again of their solubility after 1 month.

The solubility was judged by cleaning the outside of the vial and placing it beneath the white light source in the darkroom for observation with naked eye at the position of a luminous intensity of about 5,000 lux. When the sample was clear with no precipitates, it was judged that the active component was dissolved.

The results are shown in Table 4. In the table, the variations with the passage of time after storage represent the solubility when stored in the form of solution.

TABLE 4

| KRN7000 | Polysorbate 20 | Variation with the passage of time after storage (by naked eye) | |
|---|---|---|---|
| (μg/ml) | (%) | 25° C., 2 weeks | 25° C., 1 month |
| 200 | 0.1 | + | |
| 200 | 0.2 | + | |
| 200 | 0.3 | − | + |
| 200 | 0.5 | − | + |
| 200 | 1.0 | − | + |
| 200 | 2.0 | − | + |
| 200 | 4.0 | − | + |
| 200 | 8.0 | − | + |

It was found from these results that Polysorbate 20 is required to be added in an amount of 0.3% or more, and it was found from the data of 25° C. for 1 month that Polysorbate 20 alone is not satisfactory for practical use. Thus, lyophilized preparations were examined in order to maintain the solubility during storage.

(3) Examination of Forming Lyophilized Preparations

Experimental Condition

First, Polysorbate 20 was dissolved in distilled water in such concentrations as listed in Table 5. Next, 20 mg of the active component (KRN7000) was weighed and stirred in 100 ml of the Polysorbate solutions having a variety of concentrations in a heated bath to 80° C. for 20 minutes in order to form a solution. After cooling with running water, the mixture was filtered through a 0.22 μm filter, and transparent colorless glass vials having a volume of 5 ml were charged with a 1 ml portion of each of a variety of solutions and subjected to lyophilizaiton. Lyophilization was carried out under the condition of preliminary freezing at −40° C. for 2 hours and drying at −20° C. for 24 hours, 10° C. for 12 hours, and finally at 25° C. for 5 hours to give the lyophilized product. The degree of vacuum was set at 0.1 Torr or less during drying step.

After the lyophilization step, the lyophilized composition was reconstituted in 1 ml of distilled water for injection, left standing for 30 minutes, and solubility was judged when the foams generated on reconstituiton disappeared.

The solubility was judged by cleaning the outside of the vial and placing it beneath the white light source in a darkroom for observation with naked eye at the position of a luminous intensity of about 5,000 lux. When the sample was clear with no precipitates, it was judged that the active component was dissolved.

The results are shown in Table 5.

TABLE 5

| Active component (KRN7000) (μg/ml) | Polysorbate 20 (%) | Re-solubility immediately after lyophilization (by naked eye) |
|---|---|---|
| 200 | 0.5 | + |
| 200 | 1.0 | + |
| 200 | 2.0 | + |

It was found from the results that Polysorbate 20 alone was not satisfactory to a lyophilized preparation.

(4) Examination of Excipient Appropriate to Lyophilization:1

Experimental Condition

A variety of monosaccharides and disaccharides were used for examination of excipients of the lyophilized preparation. In this context, the active component (KRN7000) was set at the concentration of 200 μg/ml, and Polysorbate 20 which is used only in a limited amount from the viewpoint of safety was set at the concentration of 0.5% in the following examination.

First, Polysorbate 20 was dissolved in distilled water in a concentration of 0.5%, and the saccharides were dissolved in such concentrations as listed in Table 6. Next, 20 mg of the active component (KRN7000) was weighed and stirred in 100 ml of the solvents in a heated bath to 80° C. for 20 minutes in order to form a solution. After cooling with running water, the mixture was filtered through a 0.22 μm filter, and transparent colorless glass vials having a volume of 5 ml were charged with a 1 ml portion of each of a variety of solutions thus obtained and subjected to lyophilization. Lyophilization was carried out under the condition of preliminary freezing at −40° C. for 2 hours and drying at −20° C. for 24 hours, 10° C. for 12 hours, and finally at 25° C. for 5 hours to give the lyophilized product. The degree of vacuum was set at 0.1 Torr or less during drying step.

After the lyophilization step, the lyophilized composition was reconstituted in 1 ml of distilled water for injection, left standing for 30 minutes, and solubility was judged when the foams generated on reconstitution disappeared.

The solubility was judged by cleaning the outside of the vial and placing it beneath the white light source in a darkroom for observation with naked eye at the position of a luminous intensity of about 5,000 lux. When the sample was clear with no precipitates, it was judged that the active component was dissolved.

The results are shown in Table 6.

TABLE 6

| Excipients | Re-solubility immediately after lyophilization | Excipients | Re-solubility immediately after lyophilization |
|---|---|---|---|
| Fructose 5% | + | Lactose 5% | + |
| Fructose 10% | + | Lactose 10% | + |
| Xylitol 4.3% | + | Glucose 5% | − |
| Xylitol 8.6% | + | Glucose 10% | + |
| Sorbitol 5% | + | Mannitol 5% | + |
| Sorbitol 10% | + | Mannitol 10% | − |
| Maltose 1.5% | + | Sucrose 4.8% | − |
| Maltose 3% | + | Sucrose 9.6% | − |

It was considered from these results that sucrose, mannitol and glucose were suitable for the excipient of lyophilization.

(5) Examination of Excipient Appropriate to Lyophilization:2

Experimental Condition

The lyophilized preparations having mannitol and sucrose added thereto were observed on their variation with the passage of time.

First, Polysorbate 20 was dissolved in distilled water in a concentration of 0.5%, and the saccharides were dissolved in such concentrations as listed in Table 7. Next, 20 mg of the active component (KRN7000) was weighed and stirred in 100 ml of the solvents in a heated bath to 80° C. for 20 minutes in order to form a solution. After cooling with running water, the mixture was filtered through a 0.22 μm filter, and transparent colorless glass vials having a volume of 5 ml were charged with a 1 ml portion of each of a variety of solutions thus obtained and subjected to lyophilization. Lyophilization was carried out under the condition of preliminary freezing at −40° C. for 2 hours and drying at −20° C. for 24 hours, 10° C. for 12 hours, and finally at 25° C. for 5 hours to give the lyophilized product. The degree of vacuum was set at 0.1 Torr or less during drying step.

After the lyophilization step, the lyophilized composition was stored at 25° C. After storage for 1 month, the lyophilized composition was reconstituted in 1 ml of distilled water for injection, left standing for 30 minutes, and solubility was judged when the foams generated on reconstitution disappeared. The samples judged in solution were further stored, and judged again of their solubility after 4 months.

The solubility was judged by cleaning the outside of the vial and placing it beneath the white light source in a darkroom for observation with naked eye at the position of a luminous intensity of about 5,000 lux. When the sample was clear with no precipitates, it was judged that the active component was dissolved.

The results are shown in Table 7.

TABLE 7

| | Re-solubility after storage (by naked eye) | |
|---|---|---|
| Excipients | 25° C., 1 month | 25° C., 4 months |
| Mannitol 10% | − | + |
| Sucrose 9.6% | − | + |

It was found from these results that the lyophilized composition having mannitol or sucrose was stable than the composition containing 0.5% Polysorbate 20 solution, and still formed a solution even after storage at 250° C. for 1 month.

In order to examine a formulation which can be stored for a further longer period, the following examinations were carried out on the additives.

(6) Examination of Additives for Improving the Re-solubility During Storage (i) In the Case of Selecting Mannitol as the Excipient Experimental Condition First, Polysorbate 20 was dissolved in distilled water in a concentration of 0.5%, and mannitol and a variety of additives such concentrations as listed in Table 8. Next, 20 mg of the active component (KRN7000) was weighed and stirred in 100 ml of the solvents in a heated bath to 80° C. for 20 minutes in order to form a solution. After cooling with running water, the mixture was filtered through a 0.22 μm filter, and transparent colorless glass vials having a volume of 5 ml were charged with 1 ml portion of each of a variety of solutions thus obtained and subjected to lyophilization. Lyophilization was carried out under the condition of preliminary freezing at −40° C. for 2 hours and drying at −20° C. for 24 hours, 10° C. for 12 hours, and finally at 25° C. for 5 hours to give the lyophilized product. The degree of vacuum was set at 0.1 Torr or less during drying step.

After the lyophilization step, the lyophilized composition was stored at 25° C. After storage for 1 month, the lyophilized composition was reconstituted in 1 ml of distilled water for injection, left standing for 30 minutes, and solubility was judged when the foams generated on reconstitution disappeared. The samples judged in solution were further stored, and judged again of their solubility after 4 months.

The solubility was judged by cleaning the outside of the vial and placing it beneath the white light source in a darkroom for observation with naked eye at the position of a luminous intensity of about 5,000 lux. When the sample was clear with no precipitates, it was judged that the active component was dissolved.

The results are shown in Table 8.

TABLE 8

| | | Re-solubility after storage (by naked eye) | |
|---|---|---|---|
| Mannitol | Additives | 25° C., 1 month | 25° C., 4 months |
| 10% | — | − | + |
| 10% | Sodium deoxycholate, 1% | − | − |
| 15% | — | + | + |
| 15% | Sodium deoxycholate, 1% | + | + |
| 15% | Glycerol, 1% | + | + |
| 15% | Glycerol, 0.1% | + | + |
| 15% | PEG400, 1% | + | + |

It was found from the above-described results that when 10% mannitol was used as the excipient, re-solubility during storage was improved by adding 1% sodium deoxycholate.

(ii) In the Case of Selecting Sucrose as the Excipient

Experimental Condition

First, Polysorbate 20 was dissolved in distilled water in a concentration of 0.5%, and sucrose and a variety of additives such concentrations as listed in Table 9. Next, 20 mg of the active component (KRN7000) was weighed and stirred in 100 ml of the solvents in a heated bath to 80° C. for 20 minutes in order to form a solution. After cooling with running water, the mixture was filtered through a 0.22 μm filter, and transparent colorless glass vials having a volume of 5 ml were charged with a 1 ml portion of each of a variety of solutions thus obtained and subjected to lyophilization. Lyophilization was carried out under the condition of preliminary freezing at −40° C. for 2 hours and drying at −20° C. for 24 hours, 10° C. for 12 hours, and finally at 25° C. for 5 hours to give the lyophilized product. The degree of vacuum was set at 0.1 Torr or less during drying step.

After the lyophilization step, the lyophilized composition thus obtained was stored at 25° C. or 50° C. , or at both of these temperatures. After storage at 25° C. for 1 month or at 50° C. for 3 days, the lyophilized composition was reconstituted in 1 ml of distilled water for injection, left standing for 30 minutes, and solubility was judged when the foams generated on reconstitution disappeared. The samples judged in solution were further stored, and judged again of their solubility after storage at 25° C. for 4 months or at 50° C. for 2 weeks.

The solubility was judged by cleaning the outside of the vial and placing it beneath the white light source in a darkroom for observation with naked eye at the position of a luminous intensity of about 5,000 lux. When the sample was clear with no precipitates, it was judged that the active component was dissolved.

The results are shown in Table 9.

TABLE 9

| | | Re-solubility after storage (by naked eye) | | | |
|---|---|---|---|---|---|
| Sucrose | Additives | 25° C., 1 month | 25° C., 4 month | 50° C., 3 days | 50° C., 2 weeks |
| 9.6% | — | − | + | + | |
| 9.6% | Sodium deoxycholate, 1% | − | − | − | − |
| 9.6% | Sodium deoxycholate, 0.1% | − | + | | |
| 9.6% | Pluronic F68, 1% | − | + | | |
| 9.6% | Pluronic F68, 0.1% | − | + | | |
| 9.6% | Propylene glycol, 1% | + | | | |
| 9.6% | Glycerol, 1% | + | | | |
| 9.6% | Arginine, 0.1% | | | + | |
| 9.6% | Glycine, 0.1% | | | + | |
| 9.6% | Glycine, 1% | | | + | |
| 9.6% | Histidine, 2% | | | − | − |

It was found from the above-described results that when sucrose was used as an excipient, the re-solubility during storage was improved by the addition of sodium deoxycholate or histidine.

(iii) Addition Effects of Sodium Deoxycholate and Histidine

Experimental Condition

Addition effects of sodium deoxycholate and histidine in the absence of a sugar as the excipient was examined.

First, Polysorbate 20 was dissolved in distilled water in a concentration of 0.5%, and histidine or sodium deoxycholate in a concentration of 1.0%. Next, 20 mg of the active component (KRN7000) was weighed and stirred in 100 ml of the solvents in a heated bath to 80° C. for 20 minutes in order to form a solution. After cooling with running water, the mixture was filtered through a 0.22 μm filter, and transparent colorless glass vials having a volume of 5 ml were charged with a 1 ml portion of each of a variety of solutions thus obtained and subjected to lyophilization. Lyophilization was carried out under the condition of preliminary freezing at −40° C. for 2 hours and drying at −20°

C. for 24 hours, 10° C. for 12 hours, and finally at 25° C. for 5 hours to give the lyophilized product. The degree of vacuum was set at 0.1 Torr or less during drying step.

After the lyophilization step, the lyophilized composition thus obtained was stored at 50° C. After storage for 3 days or 2 weeks, the lyophilized composition was reconstituted in 1 ml of distilled water for injection, left standing for 30 minutes, and solubility was judged when the foams generated on reconstitution disappeared.

The solubility was judged by cleaning the outside of the vial and placing it beneath the white light source in a darkroom for observation with naked eye at the position of a luminous intensity of about 5,000 lux. When the sample was clear with no precipitates, it was judged that the active component was dissolved.

The results are shown in Table 10.

TABLE 10

| Additives | Re-solubility after storage (by naked eye) | |
|---|---|---|
| | 50° C., 3 days | 50° C., 2 weeks |
| Histidine, 1% | | + |
| Sodium deoxycholate, 1% | + | |

It was found from the above-described results that histidine or sodium deoxycholate alone exhibited no effects.

(7) Examination of Optimal Formulation

Experimental Condition

First, Polysorbate 20 was dissolved in distilled water in a concentration of 0.5%, and sucrose and histidine or sodium deoxycholate in such concentrations listed on Table 11. Next, 20 mg of the active component (KRN7000) was weighed and stirred in 100 ml of the solvents in a heated bath to 80° C. for 20 minutes in order to form a solution. After cooling with running water, the mixture was filtered through a 0.22 μm filter, and transparent colorless glass vials having a volume of 5 ml were charged with a 1 ml portion of each of a variety of solutions thus obtained and subjected to lyophilization. Lyophilization was carried out under the condition of preliminary freezing at −40° C. for 2 hours and drying at −20° C. for 24 hours, 10° C. for 12 hours, and finally at 25° C. for 5 hours to give the lyophilized product. The degree of vacuum was set at 0.1 Torr or less during drying step.

After the lyophilization step, the lyophilized composition thus obtained was stored at 25° C. or 50° C. After storage at 25° C. for 2 months or at 50° C. for 2 weeks, the lyophilized composition was reconstituted in 1 ml of distilled water for injection, left standing for 30 minutes, and solubility was judged when the foams generated on reconstitution disappeared. The samples judged to be solution after storage at 25° C. for 2 months were further stored, and judged again of their solubility after storage for 4 months.

The solubility was judged by cleaning the outside of the vial and placing it beneath the white light source in a darkroom for observation with naked eye at the position of a luminous intensity of about 5,000 lux. When the sample was clear with no precipitates, it was judged that the active component was dissolved.

The results are shown in Table 11.

TABLE 11

| Sucrose | Additives | Re-solubility after storage (by naked eye) | | |
|---|---|---|---|---|
| | | 25° C., 2 months | 25° C., 4 months | 50° C., 2 weeks |
| 19.2% | Sodium deoxycholate, 0.1% | + | | |
| 19.2% | Sodium deoxycholate, 0.2% | + | | |
| 19.2% | Sodium deoxycholate, 0.5% | + | | |
| 19.2% | Sodium deoxycholate, 1% | + | | |
| 19.2% | Sodium deoxycholate, 2% | + | | |
| 9.6% | Sodium deoxycholate, 0.2% | + | | |
| 9.6% | Sodium deoxycholate, 0.5% | − | − | |
| 9.6% | Sodium deoxycholate, 1% | − | − | |
| 9.6% | Sodium deoxycholate, 2% | − | − | |
| 4.8% | Sodium deoxycholate, 0.2% | + | | |
| 4.8% | Sodium deoxycholate, 0.5% | − | − | |
| 4.8% | Sodium deoxycholate, 1% | − | − | |
| 4.8% | Sodium deoxycholate, 2% | − | − | |
| 9.6% | Histidine, 2% | | | − |
| 7.9% | Histidine, 0.5% | | | + |
| 6.9% | Histidine, 1% | | | − |
| 5.0% | Histidine, 2% | | | − |
| 3.1% | Histidine, 3% | | | − |
| 1.1% | Histidine, 4% | | | + |
| 5.1% | Histidine, 1% | | | − |
| 3.2% | Histidine, 2% | | | − |

It was found from the above-described results that the re-solubility of the active component with the passage of time after storage under lyophilization is improved by further incorporating a suitable amount of sodium deoxycholate or histidine into polyoxysorbitan fatty acid ester and white sugar.

(8) Examination of Cooling Condition After Dissolution with Heating: 1

Experimental Condition

First, Polysorbate 20 was dissolved in distilled water in a concentration of 0.5%, histidine in a concentration of 0.75%, and sucrose in a concentration of 5.6%. Next, 800 mg of the active component (KRN7000) was weighed and stirred in 4 liters of the solvent under heating at 73° C. for 30 minutes in order to form a solution. After dissolution, the mixture was divided into about 500 ml portions, cooled with stirring from 73° C. to 30° C. (6 minutes), from 73° C. to 30° C. (23 minutes), and from 73° C. to 30° C. (120 minutes). After cooling, the mixtures were filtered through a 0.22 μm filter, and transparent colorless glass vials having a volume of 5 ml were charged with a 1 ml portion of each of a variety of solutions thus obtained and subjected to lyophilization. Lyophilization was carried out under the condition of preliminary freezing at −50° C. for 5 hours and drying at −15° C. for 48 hours, 10° C. for 12 hours, and finally at 25° C. for 7 hours to give the lyophilized product. The degree of vacuum was set at 0.1 Torr or less during drying step.

The turbidity of the solutions prepared respective cooling conditions before or after the filtration step, and the lyophilized composition thus obtained which were reconstituted after leaving standing at room temperature (25° C.) for 3 hours from the lyophilization step, were measured. In this connection, the lyophilized composition was reconstituted in 1 ml of distilled water for injection, left standing for 30 minutes, and turbidity was measured when the foams generated on reconstitution disappeared.

The turbidity was measured by the following method: various dilutions including 50-fold dilution (kaolin 2 μg/ml, turbidity 2.00), 100-fold dilution (kaolin 1 μg/ml, turbidity 1.00), and 200-fold dilution (kaolin 0.5 μg/ml, turbidity 0.50) were prepared by diluting the turbidity standard (kaolin, 0.1 mg/ml) with distilled water. A calibration curve was made by measuring the absorbance at a wave length of 660 nm with a control of distilled water and the various dilutions in a spectrophotometer (HITACHI U-3210). Next, the absorbance of the solutions was measured under the same condition as above to calculate the turbidity of the solutions.

The results are shown in Table 12.

TABLE 12

| Cooling conditions | Turbidity | | |
|---|---|---|---|
| | Before filtration | After filtration | Lyophilized composition |
| 73° C. → 30° C., 6 minutes | 0.23 | 0.13 | 0.24 |
| 73° C. → 30° C., 23 minutes | 0.58 | 0.15 | 0.36 |
| 73° C. → 30° C., 120 minutes | 0.64 | 0.16 | 0.36 |

It was found from the above-described results that the re-solubility of the active component after lyophilization was improved by rapid cooling as a cooling condition.

(9) Examination of Cooling Condition After Dissolution with Heating: 2

Experimental Condition

First, Polysorbate 20 was dissolved in distilled water in a concentration of 0.5%, histidine in a concentration of 0.75%, and sucrose in a concentration of 5.6%. Next, 800 mg of the active component (KRN7000) was weighed and stirred in 4 liters of the solvent under heating at 73° C. for 30 minutes in order to form a solution. After dissolution, the mixture was divided into about 500 ml portions, cooled rapidly—gradually with stirring under the following six rates:

| Cooling conditions | Temperature lowering time (Average temperature lowering rate) |
|---|---|
| ① 73° C. → 30° C. | 4 minutes (10.75° C./min) |
| ② 73° C. → 30° C. | 6 minutes (7.17° C./min) |
| ③ 73° C. → 30° C. | 7 minutes (6.14° C./min) |
| ④ 73° C. → 30° C. | 10 minutes (4.30° C./min) |
| ⑤ 73° C. → 30° C. | 23 minutes (1.87° C./min) |
| ⑥ 73° C. → 30° C. | 120 minutes (0.36° C./min) |

After cooling, the mixtures were filtered through a 0.22 μm filter, and transparent colorless glass vials having a volume of 5 ml were charged with a 1 ml portion of each of a variety of solutions thus obtained and subjected to lyophilization. Lyophilization was carried out under the condition of preliminary freezing at −50° C. for 5 hours and drying at −15° C. for 48 hours, 10° C. for 12 hours, and finally at 25° C. for 7 hours to give the lyophilized product. The degree of vacuum was set at 0.1 Torr or less during drying step.

After lyophilization, the lyophilized composition thus obtained was stored at 50° C. for 1 week, and the turbidity of the reconstituted solution was measured. In this connection, the turbidity of the lyophilized composition was used which was Wil: reconstituted in 1 ml of distilled water for injection and left standing for 30 minutes, and turbidity was measured when the foams generated on reconstitution disappeared.

The turbidity was measured by the following method: various dilutions including 50-fold dilution (kaolin 2 μg/ml, turbidity 2.00), 100-fold dilution (kaolin 1 μg/ml, turbidity 1.00), and 200-fold dilution (kaolin 0.5 μg/ml, turbidity 0.50) were prepared by diluting the turbidity standard (kaolin, 0.1 mg/ml) with distilled water. A calibration curve was made by measuring the absorbance at a wave length of 660 nm with a control of distilled water and the various dilutions in a spectrophotometer (HITACHI U-3210). Next, the absorbance of the solutions was measured under the same condition as above to calculate the turbidity of the solutions.

The results are shown in Table 13.

TABLE 13

| Cooling conditions | Turbidity |
|---|---|
| ① | 2.08 |
| ② | 2.67 |
| ③ | 3.31 |
| ④ | 3.80 |
| ⑤ | 6.44 |
| ⑥ | 18.84 |

It was found from the above-described results that the re-solubility of the active component with the passage of time after storage is further improved by cooling rapidly.

[Lyophilized Composition for Injection]

| Composition 1 | |
|---|---|
| α-glycosylceramide (KRN7000) | 0.2 mg |
| Polyoxysorbitan fatty acid ester (Polysorbate 20) | 5 mg |
| Mannitol | 100 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 2 | |
|---|---|
| α-glycosylceramide (KRN700) | 0.2 mg |
| Polyoxysorbitan fatty acid ester (Polysorbate 20) | 5 mg |
| Mannitol | 100 mg |
| Sodium deoxycholate | 10 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 3 | |
|---|---|
| α-glycosylceramide (KRN 7000) | 0.2 mg |
| Polyoxysorbitan fatty acid ester (Polysorbate 20) | 5 mg |
| Sucrose | 100 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 4 | |
|---|---|
| α-glycosylceramide (KRN 7000) | 0.2 mg |
| Polyoxysorbitan fatty acid ester (Polysorbate) 20) | 5 mg |
| Sucrose | 96 mg |
| Sodium deoxycholate | 5 mg |
| Solvent (distilled water for injection | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 5 | |
|---|---|
| α-glycosylceramide (KRN7000) | 0.2 mg |
| Polyoxysorbitan fatty acid ester (polysorbate 20) | 5 mg |
| Sucrose | 96 mg |
| Sodium deoxycholate | 10 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 6 | |
|---|---|
| α-glycosylceramide (KRN7000) | 0.2 mg |
| Polyoxysorbitan fatty acid ester (Polysorbate 20) | 5 mg |
| Sucrose | 96 mg |
| Sodium deoxycholate | 20 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 7 | |
|---|---|
| α-glycosylceramide (KRN7000) | 0.2 mg |
| Polyoxysorbitan fatty acid ester (Polysorbate 20) | 5 mg |
| Sucrose | 48 mg |
| Sodium deoxycholate | 5 mg |
| Solvent (distilled water for injection) | q.s. |
| Total | 1 ml |

According to the above-described formulation, (α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 8 | |
|---|---|
| α-glycosylceramide (KRN7000) | 0.2 mg |
| Polyoxysorbitan fatty acid ester (Polysorbate 20) | 5 mg |
| Sucrose | 48 mg |
| Sodium deoxycholate | 10 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 9 | |
|---|---|
| α-glycosylceramide (KRN7000) | 0.2 mg |
| Polyoxysorbitan fatty acid ester (Polysorbate 20) | 5 mg |
| Sucrose | 48 mg |
| Sodium deoxycholate | 20 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 10 | |
|---|---|
| α-glycosylceramide (KRN7000) | 0.2 mg |
| Polyoxysorbitan fatty acid ester (Polysorbate 20) | 5 mg |
| Sucrose | 75.2 mg |
| Sodium deoxycholate | 5 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 11 | |
|---|---|
| α-glycosylceramide (KRN7000) | 0.2 mg |
| Polyoxysorbitan fatty acid ester (Polysorbate 20) | 5 mg |
| Sucrose | 72.9 mg |
| Sodium deoxycholate | 10 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 12 | |
|---|---|
| α-glycosylceramide (KRN7000) | 0.2 mg |
| Polyoxysorbitan fatty acid ester (Polysorbate 20) | 5 mg |
| Sucrose | 96 mg |
| Histidine | 20 mg |
| Solvent (distilled water for injection) | q.s |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 13 | |
|---|---|
| α-glycosylceramide (KRN7000) | 0.2 mg |
| Polyoxysorbitan fatty acid ester (Polysorbate 20) | 5 mg |
| Sucrose | 69 mg |
| Histidine | 10 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 14 | |
|---|---|
| α-glycosylceramide (KRN7000) | 0.2 mg |
| Polyoxysorbitan fatty acid ester (Polysorbate 20) | 5 mg |
| Sucrose | 51 mg |
| Histidine | 10 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 15 | |
|---|---|
| α-glycosylceramide (KRN7000) | 0.2 mg |
| Polyoxysorbitan fatty acid ester (Polysorbate 20) | 5 mg |
| Sucrose | 50 mg |
| Histidine | 20 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 16 | |
|---|---|
| α-glycosylceramide (KRN7000) | 0.2 mg |
| Polyoxysorbitan fatty acid ester (Polysorbate 20) | 5 mg |
| Sucrose | 32 mg |
| Sodium deoxycholate | 20 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 17 | |
|---|---|
| α-glycosylceramide (KRN7000) | 0.2 mg |
| Polyoxysorbitan fatty acid ester (Polysorbate 20) | 5 mg |
| Sucrose | 31 mg |
| Histidine | 30 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 18 | |
|---|---|
| α-glycosylceramide (KRN7000) | 0.2 mg |
| Polyoxysorbitan fatty acid ester (Polysorbate 20) | 5 mg |
| Sucrose | 68.8 mg |
| Histidine | 10 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 19 | |
|---|---|
| α-glycosylceramide (KRN7000) | 0.2 mg |
| Polyoxysorbitan fatty acid ester (Polysorbate 20) | 5 mg |
| Sucrose | 56 mg |
| Histidine | 7.5 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

| Composition 20 | |
|---|---|
| α-glycosylceramide (KRN7000) | 0.2 mg |
| Polyoxysorbitan fatty acid ester (Polysorbate 20) | 5 mg |
| Sucrose | 51.2 mg |
| Histidine | 10 mg |
| Solvent (distilled water for injection) | q.s. |
| Total | 1 ml |

According to the above-described formulation, α-glycosylceramide (KRN7000) was completely dissolved by heating at 80° C. for 20 minutes, cooled with running water for 15 minutes, filtered through a 0.22 μm filter, and lyophilized to give a lyophilized preparation for injection.

When the solubility of the lyophilized preparations of the composition 1–20 was evaluated immediately after lyophilization and after storage with the passage of time, favorable solubility was obtained in all of the cases as shown in Table 14.

TABLE 14

| | Re-solubility after storage (by naked eye) | | | | | |
|---|---|---|---|---|---|---|
| | 25° C. | | | 40° C. | | | 50° C. |
| Compound No. | 1 month | 2 months | 4 months | 1 month | 2 months | 4 months | 2 weeks |
| 1 | — | | | | | | |
| 2 | — | — | | | | | |
| 3 | — | | | | | | |
| 4 | | — | — | | | | |
| 5 | — | — | — | — | — | — | — |
| 6 | | — | — | | — | — | |
| 7 | | — | — | | — | — | |
| 8 | | — | — | | — | — | |
| 9 | | — | — | | — | — | |
| 10 | — | — | — | — | — | — | |
| 11 | — | — | — | — | — | — | |
| 12 | | | | | | | — |
| 13 | | | | | | | — |
| 14 | | | | | | | — |
| 15 | | | | | | | — |
| 16 | | | | | | | — |
| 17 | | | | | | | — |
| 18 | — | — | — | | | | |
| 19 | — | — | — | — | — | | |
| 20 | — | — | — | — | | | |

—: clear with no precipitates.

INDUSTRIAL APPLICABILITY

According to the present invention, when a sphingoglycolipid as an active ingredient (α-glycosylceramide comprising a monosaccharide as a sugar portion) which has a low solubility in water was incorporated before lyophilization in combination with a polyoxysorbitan fatty acid ester and disaccharide (such as sucrose) or monosaccharide (such as glucose or mannitol), the solubility of the active component in a solvent is extremely improved. It is also possible to further enhance the re-solubility after storage for a long period by additionally incorporating sodium deoxycholate or histidine into the above formulation. Thus, the composition according to the present invention is useful as the lyophilized preparation for injection excellent in solubility.

What is claimed is:

1. A lyophilized composition comprising the α-glycosylceramide represented by the following formula (A) or a salt thereof; a polyoxysorbitan fatty acid ester; histidine; and a disaccharide or monosaccharide:

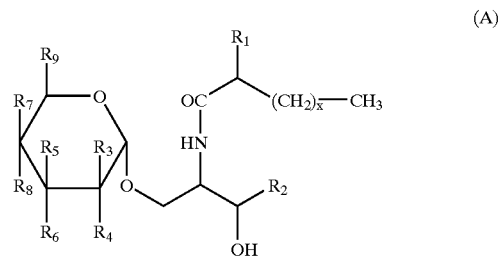

wherein
$R_1$ represents H or OH,
X denotes an integer in the range of 7–25,
$R_2$ represents any one of the substituents defined in the following (a)–(e):
(a) —$CH_2(CH_2)_YCH_3$, (b) —CH(OH)(CH$_2$)$_Y$CH$_3$,
(c) —CH(OH)(CH$_2$)$_Y$CH(CH$_3$)$_2$,
(d) —CH=CH(CH$_2$)$_Y$CH$_3$,
(e) —CH(OH)(CH$_2$)$_Y$CH(CH$_3$)CH$_2$CH$_3$,
wherein Y denotes an integer n the range of 5–17,
either one of R$_3$ or R$_4$ represents H, and the other represents H, OH, NH$_2$ or NHCOCH$_3$,
either one of R$_5$ or R$_6$ represents H, and the other represents OH,
either one of R$_7$ or R$_8$ represents H, and the other represents OH,
R$_9$ represents H, CH$_3$ or CH$_2$OH.

2. A lyophilized composition according to claim 1, which comprises the α-glycosylceramide represented by the formula (A') or a salt thereof:

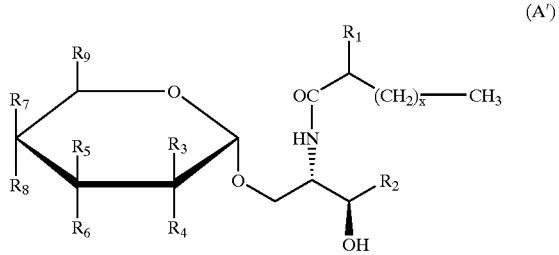

wherein
R$_1$ represents H or OH,
X denotes an integer in the range of 7–25,
R$_2$ represents any one of the substituents defined in the following (a)–(e):
(a) —CH$_2$(CH$_2$)$_Y$CH$_3$,
(b) —CH(OH)(CH$_2$)$_Y$CH$_3$,
(c) —CH(OH)(CH$_2$)$_Y$CH(CH$_3$)$_2$,
(d) —CH=CH(CH$_2$)$_Y$CH$_3$,
(e) —CH(OH)(CH$_2$)$_Y$CH(CH$_3$)CH$_2$CH$_3$,
wherein Y denotes an integer in the range of 5–17,
R$_3$–R$_9$ represent the substituents defined in the following i)–v):
i)
when R$_3$, R$_6$ and R$_8$ represent H,
R$_4$ represents H, OH, NH$_2$ or NHCOCH$_3$,
R$_5$ represents OH,
R$_7$ represents OH,
R$_9$ represents H, CH$_3$ or CH$_2$OH;
ii)
when R$_3$, R$_6$ and R$_7$ represent H,
R$_4$ represents H, OH, NH$_2$ or NHCOCH$_3$,
R$_5$ represents OH,
R$_8$ represents OH,
R$_9$ represents H, CH$_3$ or CH$_2$OH;
iii)
when R$_4$, R$_6$ and R$_7$ represent H,
R$_3$ represents H, OH, NH$_2$ or NHCOCH$_3$,
R$_5$ represents OH,
R$_8$ represents OH,
R$_9$ represents H, CH$_3$ or CH$_2$OH;
iv)
when R$_4$, R$_5$ and R$_7$ represent H,
R$_3$, R$_6$ and R$_8$ represent OH,
R$_9$ represents H, CH$_3$ or CH$_2$OH;
v)
when R$_3$, R$_5$ and R$_7$ represent H,
R$_4$, R$_6$ and R$_8$ represent OH,
R$_9$ represents H, CH$_3$ or CH$_2$OH.

3. A lyophilized composition according to claim 1, wherein R$_3$, R$_6$ and R$_8$ of the α-glycosylceramide represent H, R$_4$, R$_5$ and R$_7$ represents OH, and R$_9$ represents CH$_2$OH.

4. A lyophilized composition according to claim 1, wherein R$_2$ of the α-glycosylceramide represents substituents (b), (c) or (e).

5. A lyophilized composition according to claim 4, wherein R$_1$ of the α-glycosylceramide represents H, and R$_2$ represents the substituent (b).

6. A lyophilized composition according to claim 5, wherein X of the methylene in the alkyl group denotes an integer of 21–25, and Y in the group R$_2$ denotes 11–15.

7. A lyophilized composition according to claim 6, wherein the α-glycosylceramide is (2S,3S,4R)-1-(α-D-galactopyranosyloxy)-2-hexacosanoylamino-3,4-octadecanediol.

8. A lyophilized composition according to claim 1, wherein the disaccharide or monosaccharide is sucrose, mannitol or glucose.

9. A lyophilized composition according to claim 1, wherein the disaccharide or monosaccharide is sucrose.

10. A lyophilized composition according to claim 1, which comprises 10–1,000 parts by weight of the polyoxsorbitan fatty acid ester, and 100–10,000 parts by weight of the disaccharide or monosaccharide to 1 part by weight of the α-glycosylceramide.

11. A lyophilized composition according to claim 1, which comprises 10–1,000 parts by weight of the polyoxysorbitan fatty acid ester, 100–10,000 parts by weight of the disaccharide or monosaccharide, and 10–1,000 parts by weight of histidine to 1 part by weight of the α-glycosylceramide.

12. A lyophilized composition according to claim 1, which is a composition for injection.

* * * * *